United States Patent
Blais

(10) Patent No.: US 7,811,353 B2
(45) Date of Patent: Oct. 12, 2010

(54) ENHANCED FERTILIZER AND METHOD FOR PRODUCING SAME

(75) Inventor: Alexandre Blais, Quebec (CA)

(73) Assignee: EVL Inc. (CA)

( * ) Notice: Subject to any disclaimer, the term of this patent is extended or adjusted under 35 U.S.C. 154(b) by 0 days.

(21) Appl. No.: 11/816,764

(22) PCT Filed: Feb. 22, 2006

(86) PCT No.: PCT/CA2006/000264

§ 371 (c)(1),
(2), (4) Date: May 20, 2008

(87) PCT Pub. No.: WO2006/089416

PCT Pub. Date: Aug. 31, 2006

(65) Prior Publication Data

US 2009/0120147 A1    May 14, 2009

Related U.S. Application Data

(60) Provisional application No. 60/654,474, filed on Feb. 22, 2005.

(51) Int. Cl.
C05F 11/08 (2006.01)
(52) U.S. Cl. .................................................. 71/6; 71/9
(58) Field of Classification Search ........................ 71/6, 71/9
See application file for complete search history.

(56) References Cited

U.S. PATENT DOCUMENTS

| | | | | |
|---|---|---|---|---|
| 3,975,545 A | * | 8/1976 | Vedamuthu | 426/40 |
| 4,119,429 A | * | 10/1978 | Lovness | 71/6 |
| 4,664,919 A | * | 5/1987 | Yan et al. | 426/46 |
| 4,956,295 A | * | 9/1990 | Sudoma | 435/252.1 |
| 4,985,060 A | * | 1/1991 | Higa | 71/6 |
| 5,549,728 A | * | 8/1996 | Wozniak et al. | 71/6 |
| 5,698,028 A | * | 12/1997 | Higa | 71/11 |
| 6,025,187 A | * | 2/2000 | Penaud | 435/262.5 |
| 6,905,288 B2 | * | 6/2005 | Miyazaki | 405/128.75 |
| 6,906,239 B2 | * | 6/2005 | Carlson | 800/279 |
| 7,410,522 B2 | * | 8/2008 | Green | 71/31 |
| 2005/0020449 A1 | | 1/2005 | Blais | |

FOREIGN PATENT DOCUMENTS

| | | |
|---|---|---|
| CA | 2332187 | 7/2002 |
| KR | 2011042 | 2/2002 |

* cited by examiner

*Primary Examiner*—Timothy C Vanoy
*Assistant Examiner*—Michelle Hou
(74) *Attorney, Agent, or Firm*—Nixon Peabody LLP

(57) ABSTRACT

The present invention relates to an enhanced fertilizer. In particular, the invention relates to an enhanced fertilizer comprising fertilizer particles, lactic acid bacteria and bacteria of the Baciliaceae family. The present invention also relates to an enhancer for a fertilizer and a soil additive to enhance plant growth. Also described herein are methods for increasing growth, development or yield of a plant and methods of enhancing a soil for increasing growth, development or yield of a plant. Methods for producing the enhanced fertilizer are also described.

53 Claims, No Drawings

ENHANCED FERTILIZER AND METHOD FOR PRODUCING SAME

CROSS-REFERENCE TO RELATED APPLICATIONS

This application is a 371 National Stage of International Application No. PCT/CA2006/000264 filed on Feb. 22, 2006, which designated Canada, and which claims the benefit under 35 U.S.C. §119(e) of U.S. Provisional Application No. 60/654,474 filed on Feb. 22, 2005, the entire contents of which are incorporated herein by reference.

TECHNICAL FIELD

The present invention relates to enhanced fertilizers, to methods for increasing growth, development or yield of a plant and to methods for enhancing a soil. The present invention also relates to methods for producing such enhanced fertilizers. In particular, the present invention relates to an enhanced fertilizer comprising a combination of compatible bacterial species, the bacterial species working in cooperation, preferably synergistically, for the enhancement of plant growth, development and yield.

BACKGROUND ART

The use of fertilizers in agriculture is well established. The art and science of fertilizers is well developed and in a modern large scale agriculture, fertilizers are formulated for very specific purposes.

More recently, the role of various microbes in promoting plant growth has come under investigation. It has been found that the supply of certain types of microbes to the soil can have very beneficial results in achieving increased crop yield, increased mineral fertilizer uptake by plants roots, increased organic matter catabolism (and emphasizing other beneficial factors to the plants) and also helping to overcome some of the soil depletion which occurs as the result of the use of artificial fertilizers.

Many different types of microbes which are beneficial to the soil are already known in the art. These microbes include, for example, nitrogen fixing bacteria. Nitrogen fixing bacteria can convert (or fix) the nitrogen directly from the air into an organic nitrogen available to the plant for protein synthesis. These nitrogen fixing bacteria can also enrich the soil around the plants by leaving organic nitrogen material in the soil for later crops.

To date, the application of fertilizer and bacteria to the soil has been considered separate operations, as liquid fertilizer and especially mineral nitrogen and other mineral contained therein is toxic to bacteria in large concentration. The application of fertilizer may be done in a dry form (most common) or by spraying in a liquid form. Similarly, the application of bacteria to the soil has been suggested using a dry dormant bacteria or alternatively, by mixing the bacteria with an inert carrier. Spraying is also practiced under various conditions such as in open field, directed to plants specifically or by injection in the soil.

One of the problems with spraying is that ultraviolet rays can have a deleterious effect on bacteria and thus it is important that the conditions be controlled. In addition, the sprayed bacteria applied can be washed away by rain. Furthermore, the bacteria are often applied in a dormant state after undergoing a drying operation wherein a lot of cell damages occur and the bacteria are therefore not in their most active state. In fact, before resuming their activity, bacteria have a lag phase necessary to re-initiate the enzymatic systems or to repair the function of enzymatic systems damaged by the treatments imposed on the ferments to dehydrate them or during long conservation time. Most often, the conditions of treatments cause the ferments to only contain spores. The lag time (or lag phase) necessary for the bacteria to resume to their full activity can be more than two hours.

It would be highly desirable to be provided with an enhanced fertilizer that would permit delivery of bacteria and fertilize in a single step.

It would be highly desirable to be provided with a method for enhancing a soil as well as a method for increasing growth, development or yield of a plant.

It would also be highly desirable to be provided with a method for producing an enhanced fertilizer.

It would also be highly desirable to be provided with a method for enhancing the properties of a fertilizer or soil by applying a combination of compatible bacterial species thereto, the bacterial species working in cooperation, preferably synergistically, for the enhancement.

SUMMARY OF THE INVENTION

One aim of the present invention is to provide an enhanced fertilizer for a plant.

Another aim of the present invention is to provide a method for enhancing the growth, yield or development of a plant.

A further aim of the present invention is to provide a method for enhancing a soil for increasing the growth, yield or development of a plant grown therein.

Another aim of the present invention is to provide a method for producing an enhanced fertilizer.

Another aim of the present invention is to provide a method for enhancing the properties of a fertilizer or soil.

According to a first aspect, the present invention provides an enhanced fertilizer for a plant, the fertilizer comprising a fertilizer particle, a lactic acid bacteria and a bacteria of the Baciliaceae family. In an embodiment, the lactic acid bacteria and the bacteria of the Baciliaceae family are active upon re-hydration. In another embodiment, the lactic acid bacteria is from a family selected from the group consisting of Lactobacillaceae, Streptococcaceae, Lactococcaceae, Leuconostocs and Bifidobacteriaceae. In another embodiment, the lactic acid bacteria is from a species selected from the group consisting of *Lactobacillus acidophilus, Streptococcus lactis, Streptococcus cremoris, Streptococcus diacetylactis, Streptococcus thermophilus, Leuconostoc cremoris, Leuconostoc diacetylactis, Bifidobacterium lactis* and *Bifidobacterium brevis*. In a further embodiment, the lactic acid bacteria is from a *Lactobacillus acidophilus* species. In another embodiment, the bacteria of the Baciliaceae family is from a species selected from the group consisting of *Bacillus subtilis* and *Bacillus licheniformis*. In a further embodiment, the enhanced fertilizer further comprising a bacteria from the *Pseudomonas putida* species. In still another embodiment, the lactic acid bacteria and the bacteria of the Baciliaceae family are sprayed on the fertilizer particle, in a further embodiment, they are sprayed concurrently or independently on the fertilizer particle. In an embodiment, a first ferment comprising the lactic acid bacteria is sprayed on the fertilizer particle. In another embodiment, the ratio (L/ton) between the first ferment and the fertilizer particle is about 1. In still another embodiment, the bacterial concentration of the first ferment is between about $10^7$ to about $10^{11}$ cells per ml, and still in a further embodiment, between about $10^8$ to about $10^9$ cells per ml. In an embodiment, a second ferment comprising the bacteria of the Baciliaceae family is sprayed on the fertilizer particle. In another embodiment, the ratio (L/ton) between the second ferment and the fertilizer particle is about 1. In another embodiment, the second ferment further comprises a bacteria of the *Pseudomonas putida* species. In a further embodiment, the bacterial concentration of the second ferment is between about $10^7$ to about $10^{11}$ cells per ml, and in a further embodiment between about $10^8$ to about $10^9$ of cells per ml. In another embodiment, the enhancer comprises nutrients for the lactic acid bacteria and the bacteria of the Baciliaceae family. In an embodiment, the enhanced fertilizer can be used on a plant selected from the group consisting of hay, cotton, cauliflower, corn and soy. In an embodiment, the lactic acid bacteria and the bacteria of the Baciliaceae family are capable of adhering to the fertilizer particle, and in a further embodiment, they are either adhering directly of by being linked to a binder. In an embodiment, the lactic acid bacteria and the bacteria of the Baciliaceae family are in their exponential growth phase.

In a further aspect, the present invention provides an enhancer for a fertilizer for a plant, the enhancer comprises the lactic acid bacteria as described herein and a bacteria of a Baciliaceae family as described herein. In an embodiment, the lactic acid bacteria and the bacteria of the Baciliaceae family are capable of adhering to the particle of the fertilizer.

In still another aspect, the present invention provides a soil additive to enhance plant growth, development or yield. In an embodiment, the soil additive comprises the lactic acid bacteria described herein and the bacteria of a Baciliaceae family described herein. In another embodiment, the lactic acid bacteria and the bacteria of the Baciliaceae family are capable of adhering to the particle of a fertilizer described herein.

In still a further aspect, the present invention provides a method for enhancing the growth, development or yield of a plant, said method comprising applying the enhanced fertilizer described herein to a soil in the vicinity of the roots of the plant.

In yet another aspect, the present invention provides a method for enhancing the growth, development or yield of a plant, said method comprising applying the enhanced fertilizer described herein under the seed of the plant.

In yet a further aspect, the present invention provides a method of enhancing a soil for increasing growth, development or yield of a plant growing therein. In an embodiment, the method comprises the step of adding to the soil the enhanced fertilizer described herein.

In another aspect, the present invention provides a method for producing an enhanced fertilizer. In an embodiment, the method comprises mixing a fertilizer particle with a lactic acid bacteria and a bacteria of the Baciliaceae family. In another embodiment, a first ferment comprising the lactic acid bacteria is mixed with the fertilizer particle. In another embodiment, the ratio (L/ton) between the first ferment and the fertilizer particle is about 1. In another embodiment, the first ferment is cooled down prior to being mixed with the fertilizer particle, in a further embodiment, the first ferment is cooled down to between about 0° C. to about 12° C. or to between about 0° C. to about 5° C. In another embodiment, a second ferment comprising the bacteria of the Baciliaceae family is mixed with the fertilizer particle. In a further embodiment, the second ferment further comprises a bacteria of the *Pseudomonas putida* species. In another embodiment, the ratio (L/ton) between the second ferment and the fertilizer particle is about 1. In an embodiment, the second ferment is cooled down prior to being mixed with the fertilizer particles, and in a further embodiment, the second ferment is cooled down to between about 0° C. to about 12° C. or to between about 0° C. to about 5° C. In another embodiment, the lactic acid bacteria and the bacteria of the Baciliaceae family are in their exponential growth phase. In a further embodiment, the bacterial concentration of the first ferment is between about $10^7$ to about $10^{11}$ cells per ml, and in a further embodiment, the bacterial concentration of the first ferment is between about $10^8$ to about $10^9$ cells per ml. In another embodiment, the bacterial concentration of the second ferment is between about $10^7$ to about $10^{11}$ cells per ml, and in a further embodiment, the bacterial concentration of the second ferment is between about $10^8$ to about $10^9$ cells per ml. In an embodiment, the lactic acid bacteria is from a family selected from the group consisting of Lactobacillaceae, Streptococcaceae, Lactococcaceae, Leuconostocs and Bifidobacteriaceae. In a further embodiment, the lactic acid bacteria is from a species selected from the group consisting of *Streptococcus lactis, Streptococcus cremoris, Streptococcus diacetylactis, Streptococcus thermophilus, Leuconostoc cremoris, Leuconostoc diacetylactis, Lactobacillus acidophilus, Bifidobacterium lactis* and *Bifidobacterium brevis*. In another embodiment, the lactic acid bacteria is from a *Lactobacillus acidophilus* species. In a further embodiment, the bacteria of the Baciliaceae family is from a species selected from the group consisting of *Bacillus subtilis* and *Bacillus licheniformis*. In yet another embodiment, nutrients for the lactic acid bacteria and the bacteria of a Baciliaceae family are mixed with the fertilizer particles. In still another embodiment, the lactic acid bacteria and the bacteria of a Baciliaceae family are sprayed on the fertilizer particles. In another embodiment, the lactic acid bacteria and the bacteria of a Baciliaceae family are sprayed concurrently or independently on the fertilizer particles.

For the purpose of the present invention the following terms are defined below.

The term "ferment" is intended to mean the product of a fermentation of an organic substrate by a bacterial strain. This product can take up any form, but is preferably in a liquid form and can easily be pulverized or atomized. The term "mixed ferment" is intended to mean the product of a fermentation of an organic substrate by more than one bacterial strain. This product can take up any form, but is preferably in a liquid form and can easily be pulverized or atomized.

As used herein, the term "fermentation" relates to a controlled transformation, usually enzymatic, more preferably by a bacteria, of an organic substrate.

The term "active bacterial strain" is intended to mean a bacterial strain that can reinitiate rapidly fermentation, with little or no lag phase (usually less than two hours to reinitiate active multiplication and growth).

The term "fertilizer" is intended to mean agglomerated solid particles of chemical substances. In an embodiment, the particles of the fertilizer may contain any, a combination of or all of nitrogen (N), phosphate (P) and potassium (K). The term "fertilizer particle" is the solid matter that makes up the fertilizer. The fertilizer particle may contains any, a combination of or all of nitrogen (N), phosphate (P) and potassium (K). The particles contained in a fertilizer may be homogenous, partly homogenous, partly heterogenous or heterogenous with respect to their nitrogen (N), phosphate (P) and potassium (K) content.

The term "enhancing the growth, yield or development of plant" is intended to mean the ability of a substance to favour, accelerate or increase plant growth, plant development or plant yield.

The term "enhancing a soil" is intended to mean the action of enriching a soil to favour, accelerate or increase plant growth, plant development or plant yield.

The term "binder" is intended to mean an inert material that is used to bind the bacteria to the fertilizer particle. For example, talc could be used as a binder. The term "talc" is the usual name of a powder of natural silicate of magnesium. The term "talc" is also intended to mean any powder medium having a good and fast hygroscopic absorbance power. In the agriculture art, talc is used frequently as a binder, especially in the field of pesticide. Talc usually rapidly fixes water.

DETAILED DESCRIPTION OF THE PREFERRED EMBODIMENTS

Different microbes, for example different bacteria, can produce different enzymes. These differences are beneficial in instances of symbiosis. Agriculturally and industrially, such enzymatic differences can be applied complementarily in processes of biodegradation of biological material or incomplete catabolism by blockage of accumulated secondary radicals in the biodegradation of proteins, fatty acids, complex sugars of aromatic and cyclic derivatives or toxic substances. Different microbes can also play different roles in active transport of certain mineral elements. These differences can be exploited by employing microbial cocktails or diverse mixtures containing combinations of two or more different but compatible bacterial species that work together in cooperation, preferably synergistically, to accelerate not only the degradation of organic material and toxic substances but of release of soluble and assimilatable nutrients and mineral elements present in the fertilizer and/or to increase uptake of assimilatable nutrients and mineral elements by a plant.

According to the present invention, desired bacterial species, from mother stocks of the same, are first subjected to a fermentation process and then combined with the fertilizer. The various bacterial species are either cultured (incubated) separately or together as a co-culture. Typically, the bacterial fermentation process takes place in an appropriate culture medium where desired nutrients enable the growth of the bacteria. This culture medium should contain a source of carbohydrate (such as lactose, sucrose or glucose) to support bacterial cell growth, a source of proteins that can be easily metabolized by the bacteria (soy, peptones, milk proteins, fish proteins or animal proteins) and a source of minerals. The culture medium chosen should not inhibit the growth of the bacteria. In an embodiment, the culture medium is a protein-fortified whey (such as a whey containing 5% of dried matter) or a milk powder-based culture medium.

When bacteria are first placed in a culture medium, they usually show a period of dormancy of up to two (2) hours, where little or no bacterial multiplication is observed. This first growth phase is called by those skilled in the art the lag phase. Then, the bacteria usually enter a period of logarithmic or exponential reproduction (exponential growth phase) until the bacterial population reaches a concentration of approximately $10^7$ to $10^{11}$ cells/ml (preferably between $10^8$ to $10^9$ cells/ml). After they reach this concentration, the bacteria usually enter a growth plateau stage and usually exhibit a slow down in multiplication. In the art, this growth plateau stage is usually explained by a lack of nutrients or an accumulation of toxic fermentation by-products.

The bacteria that are present in the enhanced fertilizer were cultured until they reach the exponential growth phase but before they reach the growth plateau stage. In an embodiment, the bacterial concentration of the ferment added to the fertilizer particles is between about $10^7$ to $10^{11}$ cells per ml, and preferably about $10^8$ to $10^9$ cells per ml. As shown herein, the use of bacteria that are in their exponential growth phase for combination with the fertilizer ensures that, after the enhanced fertilizer is applied to a soil (and hence the bacteria are re-hydrated), they resume their growth and/or metabolic activity (less than two hours).

The enhanced fertilizer (and related methods) can comprise various bacterial species, but more preferably those that can have a beneficial effect on plants or crop growth, yield or development. The particular type of bacteria or microbe which may be used with the present invention may be any known desirable type of bacterial species which can successfully undergo the above treatment. Such known bacterial species include nitrogen fixing bacteria, microbes used in soil bioremediation, microbes used in the dairy industry, etc.

One advantage of the compositions and methods described herein is the fact that the microbes are in a healthy state when they are mixed to the regular fertilizer. The bacterial cells are thus minimally damaged by the methods described herein and may resume their growth and/or metabolic activity upon rehydration. There is a minimal lag time for bacterial growth as compared to other methods and compositions known in the art.

In an embodiment, the enhanced fertilizer comprises a fertilizer particle, a lactic acid bacteria and a bacteria of the Baciliaceae family. The lactic acid bacteria may be, for example, of the Lactobacillaceae, Streptococcaceae, Lactococcaceae, Leuconostocs, and/or the Bifidobacteriaceae family. The species of the lactic acid bacteria may be, for example, *Lactobacillus acidophilus, Streptococcus lactis, Streptococcus cremoris, Streptococcus diacetylactis, Streptococcus thermophilus, Leuconostoc cremoris, Leuconostoc diacetylactis, Bifidobacterium lactis*, and/or *Bifidobacterium brevis*. The species of the bacteria of a Baciliaceae family may be, for example, a coagulase negative *Bacillus cereus, Bacillus subtilis*, and/or *Bacillus licheniformis*. Bacteria of the Baciliaceae family may produce many exoenzymes. A person skilled in the art will realize that it is necessary to avoid the use of Bacillus strains capable of producing haemolysin, as well as those strains having septicemic properties for health reasons. In another embodiment, the enhanced fertilizer may further comprise a bacteria having beneficial effects on plant growth, yield and development. In an embodiment, the bacteria can be from the *Pseudomonas putida* species. The bacteria of the *Pseudomonas putida* species is frequently used in bioremediation processes. It can make up to about 8 to 9% of the co-culture, and exert positive and beneficial action in the absorption of minerals for plants. It can also facilitate the degradation of toxic substances like hydrocarbons and other pollutants that may be present in the soil.

The enhanced fertilizer described herein comprises a lactic acid bacteria and a bacteria of the Baciliaceae family. Prior to their combination with the fertilizer particles, the lactic acid bacteria and the bacteria from the Baciliaceae family can be grown separately or in co-culture. In an embodiment, more than one species of lactic acid bacteria can be combined with the regular fertilizer and the bacteria from the Baciliaceae family. Prior to their combination with the fertilizer particles and the bacteria from the Baciliaceae family, the various species of lactic acid bacteria can be grown separately or in co-culture. In an embodiment, more than one species of bacteria from the Baciliaceae family can be combined with the fertilizer particles and the lactic acid bacteria. Prior to their combination with the fertilizer particles and the lactic acid bacteria, the various species of bacteria from the Baciliaceae can be grown separately or in co-culture. In another embodiment, a bacteria from the *Pseudomonas putida* species can be combined with the fertilizer particles, the lactic acid bacteria (or the various species of lactic acid bacteria) and the bacteria of the Baciliaceae family (or the various species of bacteria of the Baciliaceae family). Prior to its combination with the fertilizer particles, the lactic acid bacteria and the bacteria of the Baciliaceae family, the bacteria of the *Pseudomonas putida* species can be grown separately or in co-culture.

The bacteria grown in a co-culture fermentation process should be "compatible". As used herein, the term "compatible" relates to the ability of various bacterial species to grow together without adversely affecting their respective growth properties or biological activity.

The various bacteria species can also be grown in separate fermentation processes and later combined with the fertilizer particles.

The bacteria combined with the fertilizer particles must be able to retain their respective growth properties or biological activity when they are applied to the soil.

In an embodiment, one preferably selects bacteria capable of resuming their growth and/or their metabolic activities once applied to the soil. In order to achieve this result, the bacterial growth in a fermentation process may be blocked once the bacteria reach their exponential growth phase. This blockage can be achieved by cold or any other means known in the art.

After the fermentation process has proceeded to a point where the bacterial population is in the range of $10^7$ to $10^{11}$ cells per ml (preferably between $10^8$ to $10^9$ cells per ml), the bacterial cells are taught to reach to their full maximum potential development. At this point in time, the fermentation is preferably subjected to an action to stop bacterial multiplication. The fermentation is preferably stopped rapidly (e.g. within an hour, within 30 minutes or preferably between 10 and 25 minutes). When a fermentation process is stopped rapidly, damages caused to the bacteria of the ferment are minimal, and the bacteria do not tend to transform into a dormant stage or spores. Therefore, when the fermentation process is stopped rapidly, the bacteria present in the ferment reactivate more rapidly upon re-hydration after they have been mixed with the fertilizer particles. In an embodiment, the ferment is preferably brought to a temperature of between 0° C. to 12° C., and more preferably to a temperature of between 0° C. and 5° C. To bring down the temperature of the ferment, the fermentation process can be cooled down with any cooling means known in the art. In an embodiment, the ferment can be placed in an ice bath. In an embodiment, when the bacterial concentration is appropriate, the ferments can be sprayed directly on the fertilizer particles thereby cooling the ferments' temperature. The ferments can also be sprayed into fine droplets on an absorbent material to dehydrate the bacteria very rapidly such that multiplication is no longer possible. Alternatively, cooling may be achieved by diafiltration or rapid centrifugation in buffered medium. Furthermore, one skilled in the art could also use a rapid cryogenic method with cryo-protectants, where sublimation following the cryogenization of a liquid phase would mimic a pseudo-lyophilization. The bacteria dried by this method may then be re-hydrated just prior to being sprayed on the fertilizer. The cooling techniques described herein are aimed at preventing bacterial stress (thereby causing sporulation or entry in a dormant stage), and at ensuring that the bacteria remain fully active and functional upon re-hydration, with a minimal lag time.

The ferments where the bacterial multiplication has been blocked can be applied on dried granular fertilizer. In an embodiment, the bacterial ferments are vaporized on dry fertilizer particles. Depending on their respective physical/chemical properties, the fertilizer particles can enable a very fast dehydration of bacterial droplets of the ferments. In return, the fast dehydration of bacterial droplets favours the viability and activity of the bacteria, thus allowing the bacteria to resume their activity rapidly when they are re-hydrated again (e.g. when the enhanced fertilizer is applied to the soil).

After rapidly cooling the ferment, the ferment is preferably combined within 72 hours, and more preferably within 48 hours, on fertilizer particles. In an embodiment, the ferment is sprayed on fertilizer particles. Individual ferments of separate bacterial species can be applied together, either by mixing the individual ferments prior to or during application or by applying the individual ferments at the same time (concurrently), for example, by spraying from separate sprayers. Alternatively, the individual ferments can be applied separately or sequentially (independently).

If a higher concentration needs to be applied on the fertilizer particles (e.g. higher than $10^8$ to $10^9$ cells per ml), the ferment can be subjected to a concentration step, such as dia-centrifigation, to increase its concentration to about $10^{10}$ cells per ml.

At this point in time, in one embodiment, a co-culture (or mix) ferment or separate individual ferments of separate bacterial species is/are then sprayed on a solid fertilizer particle such that the bacteria will adhere to the fertilizer particle. Ferments of separate bacterial species can be applied together, either by mixing the separate ferments prior to or during application, or by applying the separate ferments at the same time, for example by spraying from separate sprayers. Alternatively, the separate ferments can be applied independently of each other. The fertilizer particle, being relatively dry, will absorb the bacterial particle and the moisture will be dispersed throughout and the bacteria will remain in a latent stable state. Ferments should be sprayed on the fertilizer particles at a rate between 0.2 to 4.0 l/tons of fertilizer particles, or preferably about 2.0 l/tons of fertilizer particles. Spraying at a higher rate can cause the chemical of the fertilizer to partly solubilize, liberating nitrogen concentrated at the surface of the fertilizer, in the vicinity of the bacteria, which is toxic to the bacteria in such concentrated micro-environment. Preferably, the ferment is sprayed at a rate of 0.5 to 2.0 l/ton, and most preferably at 2.0 l/ton on the fertilizer.

In a further and different aspect of the present invention, the ferment may be sprayed on a seed particle.

In lieu of spraying, ferments may also be applied by means of a binding agent such as starch or talc, or any other suitable product which would function to bind the bacteria to the seed product. Powdered milk is particularly well suited for such application. In fact, any dry powder, such as talc, flour, sugars, starch or powdered milk, can be supplemented with a binding agent such as oil or milk fat for example to enable the dry powder to bind bacteria and the fertilizer. The dry powder that can be used in accordance with the present invention are thus those that can absorb by contact humidity, that are non-toxic to the bacteria and that may act as a binder. Once the bacteria has adhered to the binder, it can be combined with the fertilizer prior to the application to the soil or before the application to the soil.

In the above process, the fertilizer may be any desired. As aforementioned, the fertilizer product absorbs the excess moisture and to this end, the fertilizer may be formulated to have this capability. Naturally, the fertilizer product will normally have a volume at least several times larger than a particle of liquid ferment. In other words, liquid ferment can be atomized and sprayed onto the fertilizer product with the moisture being absorbed over the whole of the fertilizer product and thus dehydrating the bacteria and rendering those into a latent stable state while still being relatively healthy with little cell damage. As such, the bacteria then remain stable and active and ready to resume their activity under the proper conditions of re-hydration in the soil.

In one particular embodiment, the concentration of the nutritive element in a ferment may be adjusted such that it remains in the ferment, at the moment where the fermentation process is stopped, a certain quantity of a nutrient material. This nutritive material with the microbes can then be sprayed on the fertilizer particle. When the fertilizer particle is hydrated in the soil, the bacteria or microbe will then resume its activity and this under desirable conditions where the nutritive material is readily available. Naturally, the nutritive material is also available for use in the soil.

The nutritive material in the fermentation approach can be selected from any number of known materials including different milk, any ingredients normally used and recognized in fermented media for fermentation purpose of any microbial culture, including synthetics media, or animal and fish by-products as well as sugars and the like.

In a further and different aspect of the present invention, ferment, either as a mix ferment or separate ferments of separate bacterial species, may be applied directly to soil, whether fertilized or not, as a soil additive to enhance the growth or yield of a plant growing in such soil. When ferment is rehydrated in the soil, the bacteria or microbe will then resume their activity, to accelerate degradation of organic material or toxic substances, or to release soluble and assimilatable nutrients and mineral elements for use by a plant or to increase uptake of assimilatable nutrients and mineral elements by a plant. Naturally, the nutritive material is also available for use in the soil.

In a further aspect of the present invention, the enhanced fertilizer described herein can be applied before, after or concurrently with any other conventional fertilizer.

In another aspect, the present invention provides an enhancer for a fertilizer for a plant. The enhancer may comprise a lactic acid bacteria and a bacteria of a Baciliaceae family. The lactic acid bacteria and the bacteria of the Baciliaceae family must be adapted in order to adhere to the particle of the fertilizer. This adaptation may include, for example, that the lactic acid bacteria and the bacteria of the Baciliaceae family may be fixed to a binder molecule capable of binding the fertilizer. The enhancer can be mixed with the fertilizer before application to the soil. The enhancer can be applied to the soil prior to, at the same time or after a fertilizer is applied to the soil.

In a further aspect, the present invention provides a soil additive to enhance plant growth, development or yield. The soil additive may comprise a lactic acid bacteria and a bacteria of a Baciliaceae family. The lactic acid bacteria and the bacteria of the Baciliaceae family must be adapted in order to adhere to the particle of the fertilizer. This adaptation may include, for example, that the lactic acid bacteria and the bacteria of the Baciliaceae family may be fixed to a binder molecule capable of binding the fertilizer or may be encapsulated in a material capable of binding the fertilizer. The soil additive can be mixed with the fertilizer prior to their application to the soil. The soil additive can be applied to the soil prior to, at the same time or after a fertilizer is applied to the soil.

A further advantage of the present invention is to provide a method for the delivery of bacteria to the soil, precisely on or close to where fertilizer particles are in the soil, preventing dispersion of the bacteria in the total mass of soil, and having a locally increased concentration of bacterial cells in close proximity to the fertilizer particles.

In one embodiment, the methods described herein provide for the use of a plurality of spraying steps to spray a fertilizer, soil or seed with the bacteria. In this respect, one uses two or more different types of bacteria, each selected for their known enzymatic or functional properties for producing interesting or beneficial results on a fertilizer, soil, seed. This possibility thus permits one to have two or more different fermentation processes under different fermentation conditions. Thus, as known in the art, there are different parameters for different types of microbes and one could thus run separate multiple fermentation processes under different conditions while spraying fertilizer, soil or seed particles sequentially, or together. When multiple ferments are used, the multiple ferments can be sprayed independently or concurrently, in which case, they are preferably mixed together just prior to spraying on the fertilizer, soil or seed.

For the application to the soil, conventional equipment may be used and thus expenses are minimized and the process is accomplished in a single operation further saving money.

As aforementioned, it is also highly advantageous that the microbes are applied to the soil in a good condition and ready to resume growth (minimal lag time) when the soil is hydrated.

The enhanced fertilizer can be applied to any plant. For example, the enhanced fertilizer can be applied to leafy plants, fruits, vegetables, plants used in ornamental gardening, lawn grass, cereals, flowers, trees and shrubs. The enhanced fertilizer can be applied on a variety of products which include hay, cabbage, coffee plant, hevea celery, cabbage, potato, lettuce, cucumber, rice, corn, soy, cauliflower and cotton for example. All of the above plants exhibited an increase or a better yield.

The fertilizer particles are a favourable environment to catch the humidity of the ferment droplets rapidly. However, there are other granular or powder products available which can do the same thing. Examples are talc, sugars, flours and any other absorbent material such as commercial absorbent products capable of dehydrating ferment droplets very quickly and make it so that the final hydration of the mixture is such that the residual humidity does not allow any growth or even any metabolic activity up until the resulting product comes into contact again with sufficient humidity as to start up the metabolism again. Such talc, sugars, flours and other absorbent materials can be mixed with the fertilizer to adhere thereto.

The applications are numerous since by choosing granular or powder absorbent products having adhesive properties, powders or particles may be enriched by concentrated ferments obtained by neutralization or concentration processes such as ultrafiltration or the like and finally mixed, for example, to soils, fertilizers or seeds. This process may be applied to soils, fertilizers or seeds simply by using mechanical mixers and the ferment enriched powders may be produced in a central point separate from fertilizer plants. This lowers investment needs. Furthermore, each of the ferment constituents of a mix may be reproduced separately and then, after having controlled their concentration, may be mixed together with precision. This modified technology may apply to compost and any material utilized in agriculture. For example, the method of the present invention can be used for coating seeds, or treating soil with a microorganism or microorganism mixture, or cocktail, if so desired.

According to a further aspect, the present invention provides a method of enhancing a soil for increasing growth, development or yield of a plant growing therein. The method comprises the step of adding to the soil the enhanced fertilizer described herein.

In still another aspect, the present invention provides a method for producing an enhanced fertilizer. The method comprising mixing a fertilizer particle with a lactic acid bacteria and a bacteria of the Baciliaceae family. In an embodiment, the lactic acid bacteria is present in a first ferment. This first ferment is mixed with the fertilizer particles at a ratio of about 1 L of ferment per ton of fertilizer. Preferably, the first ferment is cooled down (to about 0° C. to 12° C. or to about 0° C. to 5° C.) prior to being mixed with the fertilizer particles, to ensure that the bacteria resume their growth and metabolic activity upon re-hydration. In another embodiment, the bacteria of the Baciliaceae family is present in a second ferment. This second ferment may also contain bacteria of the *Pseudomonas putida* species. This second ferment is mixed with the fertilizer particles at a ratio of about 1 L of ferment per ton of fertilizer. Preferably, the second ferment is cooled down (to about 0° C. to 12° C. or to about 0° C. to 5° C.) prior to being mixed with the fertilizer particles, to ensure that the bacteria resume their growth and metabolic activity upon re-hydration. Prior to their combination with the fertilizer particles, the lactic acid bacteria and the bacteria of the Baciliaceae family are preferably in their exponential growth phase. The bacterial concentration of the first ferment and the second is between about $10^7$ to about $10^{11}$ cells/ml. In an embodiment, nutrients for the lactic acid bacteria and the bacteria of a Baciliaceae family can be mixed with the fertilizer particles. In another embodiment, the lactic acid bacteria and the bacteria of a Baciliaceae family are sprayed on the fertilizer particles, and preferably, sprayed concurrently on the fertilizer particles.

The present invention will be more readily understood by referring to the following examples which are given to illustrate the invention rather than to limit its scope.

Example I

Preparation of the Enhanced Fertilizer

Ferment I contained only *Lactobacillus acidophilus*. *Lactobacillus acidophilus* was incubated at a temperature of about 30±3° C. in a whey-based culture medium. This bacteria can be incubated at other temperatures from 5° C. up to its maximum lethal temperature. One of skill in the art will realize that when other strains are used, different optimum temperature and growth ranges will vary accordingly.

Ferment II contained *Bacillus subtilis, Bacillus licheniformis* and *Pseudomonas putida*. *Bacillus subtilis, Bacillus licheniformis* and *Pseudomonas putida* were co-cultured at a temperature of about 27±2° C. in a whey-based culture medium. The non-sporulating form of the *Bacillus* family members were chosen because they are in their most active state. The bacteria can be incubated at other temperatures within their growth ranges. One of skill in the art will realize that when other strains are used, the optimum growth temperature and growth ranges will vary accordingly.

Once the bacterial cultures reached $10^8$-$10^9$ bacterial cells per ml, ferment I and II were cooled (with an ice bath) and sprayed concurrently on fertilizer particles. The fertilizer being sprayed may be any mineral fertilizer recommended by a field fertilizer specialist according to results of the soil analysis for a specific plant. Each ferments were atomized separately and sprayed concurrently on moving fertilizer particles. Table I indicates the various combinations of the ferments sprayed on the fertilizer used in the following examples.

TABLE 1

Combinations of sprayed ferments I and II per ton of fertilizer

| Combination | Litres of ferment I | Litres of ferment II |
|---|---|---|
| A | 0 | 0 |
| B | 0 | 2 |
| C | 1 | 1 |
| D | 2 | 0 |
| E | 0.5 | 1.5 |

Example II

Application of the Enhanced Fertilizer on Hay and Cotton

For the hay field trails, a fertilizer having a N-P-K of 20-13-19 was sprayed with the combination C described in Example I. A control fertilizer not sprayed with the combination was also used. Both fertilizers were then were at a rate of 100 kg/acre in field trials on a hayfield where a mineral fertilizer was previously applied at 100 kg/acre. The treatments were done in duplicate.

At the time of cutting the hay, the results show that combination C of each of the ferments generated the best results. At the time of cutting, the hay treated with combination C was darker and it was almost reaching 6 inches in height. Once the combination C was applied, the hay was greener and healthier than the untreated hayfield (hay treated with unsprayed fertilizer). These results indicate a synergistic interaction between the different bacterial strains present in the combination.

For the cotton field trails, a fertilizer having a N-P-K of 20-13-19 containing 2 kg of sulfur of was sprayed with the combination described in Example I. The fertilizer was then were applied in cotton fields. The treatments were done in duplicate. Applications of the fertilizer sprayed with combination B, D and E results in some benefit for the cotton, but inferior and less regular than the results obtained with combination C. These results also show the synergy between the ferments used in the fertilizer.

Example III

Bacterial Viability Testing

In order to verify that the bacteria sprayed on the fertilizer were viable, the coated fertilizer (50 g) was solubilized in 40 liters of sterile phosphate buffer. The solubilized fertilizer was then subjected to ultrafiltration using a second 40 liters of phosphate buffer. The filtrate was then been incubated on LBS and MRS. The results indicated that the bacteria were indeed able to resume their growth.

Example IV

Effect of the Enhanced Fertilizer on the Growth and Development of Cauliflower

The field trials have been taken place in the Boson commune (BacNinh town, Bac ninh province, Vietnam). The cauliflowers studied were of the Chinese variety. The cauliflowers grew between 85 to 90 days (including the nursery time). The cauliflowers were transplanted on Nov. 3, 2005 and harvested on Jan. 23, 2006. The plant spacing was 70 cm by 40 cm. The density was 36,000 plants per hectare. The plants were treated five times, the design was repeated 4 times. The size plot was 24 m². Table 2 indicates the total fertilizer used in the various treatment.

TABLE 2

Total fertilizer (kg/ha) used in the experimental treatments

| Treatment | Combination sprayed on the fertilizer (as described in Example I) | FYM fertilizer | N | $P_2O_5$ | $K_2O$ |
|---|---|---|---|---|---|
| 1 | C | 0 | 180 | 180 | 180 |
| 2 | B | 0 | 180 | 180 | 180 |
| 3 | D | 0 | 180 | 180 | 180 |
| 4 | A | 0 | 180 | 180 | 180 |
| 5 | None | 5000 | 150 | 120 | 150 |

The combination were sprayed on the fertilizer described in table 2 only for the basal application. For treatments 1 to 4, a first basal application (20% of the total fertilizer) of the fertilizer sprayed with the various combinations was applied just under the planted seeds. A first top dressing of 15 kg/ha diammonium phosphate (DAP) and 40% of the total fertilizer (not sprayed) were applied side hill 15 days after seedling. A second top dressing of 35 kg/ha diammonium phosphate (DAP) and 20% of the total fertilizer (not sprayed) was applied side hill 35 days after seedling. A third top dressing of 5 kg/ha diammonium phosphate (DAP) and 20% of the total fertilizer (not sprayed) were applied side hill 50 days after seedling.

For treatment 5 (control), a first basal application of the FYM fertilizer (a combination of composted manure and vegetal residues), 50 kg/ha $P_2O_5$, 20 kg/ha N and 20 kg/ha $K_2O$ were applied just under the planted seeds. A first top dressing of 15 kg/ha diammonium phosphate (DAP) 40 kg/ha and 40 kg/ha $K_2O$ were applied side hill 15 days after seedling. A second top dressing of 35 kg/ha diammonium phosphate (DAP), 50 kg/ha $P_2O_5$, 20 kg/ha N and 20 kg/ha $K_2O$ were applied side hill 35 days after seedling. A third top dressing of 50 kg/ha diammonium phosphate (DAP), 20 kg/ha N and 20 kg/ha $K_2O$ were applied side hill 50 days after seedling.

After the treatment, the cauliflower were harvested and several parameters were measured. Table 3 shows the harvesting data for the total biomass (stem, leaf and flower) and the flower mass of the harvested cauliflowers. Table 4 shows the effects of the treatments on the cauliflower biomass (CV % is 4.43, LSD0.05 is 0.61) and on the cauliflowers flower mass (the marketable product, CV % 4.78, LSD0.05 0.25).

Plants treated with combination C (treatment 1) not only had the highest total biomass but also the highest flower mass, hence the highest marketable index. The marketable product index of plants treated with combination C is increased by more than 14% with respect to the control treatment (treatment 5). The marketable product index of plants treated with combination (treatment 2) is increased by more than 12% with respect to the control treatment (treatment 5).

TABLE 3

Harvesting data

| Treatment | Rep I | Rep II | Rep III | Rep IV |
|---|---|---|---|---|
| | Total biomass (ton/ha) | | | |
| 1 | 92.35 | 87.12 | 91.25 | 88.06 |
| 2 | 84.29 | 91.20 | 87.26 | 90.43 |
| 3 | 81.06 | 83.70 | 83.38 | 85.46 |

TABLE 3-continued

Harvesting data

| Treatment | Rep I | Rep II | Rep III | Rep IV |
|---|---|---|---|---|
| 4 | 85.11 | 87.90 | 86.26 | 88.42 |
| 5 | 81.40 | 81.50 | 77.76 | 68.22 |
| | Flower biomass (ton/ha) | | | |
| 1 | 40.24 | 39.85 | 36.66 | 36.99 |
| 2 | 37.85 | 37.39 | 36.65 | 38.88 |
| 3 | 32.83 | 31.81 | 33.02 | 34.18 |
| 4 | 31.49 | 35.14 | 33.19 | 34.48 |
| 5 | 31.75 | 27.71 | 28.77 | 27.29 |

TABLE 4

Mean cauliflower biomass and flower mass and marketable index

| Treatment | Total biomass (ton/ha) | Total flower mass (ton/ha) | Marketable index* |
|---|---|---|---|
| 1 | 89.70 | 38.44 | 0.429 |
| 2 | 88.30 | 37.69 | 0.427 |
| 3 | 83.40 | 32.96 | 0.395 |
| 4 | 86.92 | 33.58 | 0.386 |
| 5 | 77.22 | 28.88 | 0.375 |

*(Total flower mass/Total biomass)

Example V

Application of the Enhanced Fertilizer on Corn and Soy Crops

For the corn field trial, combination C described in Example I was sprayed on either the fertilizer (purchased from Synagri) having a N-P-K of 20-10-20 (herein referred to as "TOTAL") or a fraction of the fertilizer containing calcium, magnesium and various fillers (herein referred to as the "FRACTION"). The fertilizer was then applied, in field beside normal seeding procedure, on a corn field at a concentration of 325 kg/acre.

For the soy field trial, combination C described in Example I was sprayed on either the fertilizer (purchased from Synagri) having a N-P-K of 15-20-20 (herein referred to as "TOTAL") or a fraction of the fertilizer containing calcium, magnesium and various fillers (herein referred to as "FRACTION"). The fertilizer was then applied on a soy field at a concentration of 140 kg/acre Corn and soy crops were harvested and their total biomass was measured. Tables 5 and 6 show the raw harvested data obtained.

TABLE 5

Corn harvested data

| Treatment | Rep I (ton/ha) | Rep II (ton/ha) | Total (ton/ha) |
|---|---|---|---|
| | Site I | | |
| Unsprayed | 10.2 | 11.9 | 11.1 |
| TOTAL | 9.2 | 11.8 | 10.5 |
| FRACTION | 10.5 | 12.2 | 11.3 |

TABLE 5-continued

Corn harvested data

| Treatment | Rep I (ton/ha) | Rep II (ton/ha) | Total (ton/ha) |
|---|---|---|---|
| Site II | | | |
| Unsprayed | 10.1 | 9.0 | 9.5 |
| TOTAL | 9.3 | 8.5 | 8.9 |
| FRACTION | 10.2 | 10.2 | 10.2 |

TABLE 6

Soy harvested data

| Treatment | Rep I (ton/ha) | Rep II (ton/ha) | Total (ton/ha) |
|---|---|---|---|
| Site I | | | |
| Unsprayed | 4.9 | 4.9 | 4.9 |
| TOTAL | 5.4 | 5.6 | 5.5 |
| FRACTION | 5.4 | 5.4 | 5.5 |
| Site II | | | |
| Unsprayed | 3.7 | 3.2 | 3.7 |
| TOTAL | 3.7 | 3.0 | 4.1 |
| FRACTION | N.A. | N.A. | N.A. |

The total biomass of the corn crops treated with a fertilizer (total or fraction) sprayed with combination C increased between 1.8 and 7% with respect to the total biomass of the control corn (treated with unsprayed fertilizer). The total biomass of the soy crops treated with a fertilizer (total of fraction) sprayed with combination C increased by about 10% with respect to the total biomass of the control soy (treated with unsprayed fertilizer).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A fertilizer for a plant, said fertilizer comprising:
   (a) a fertilizer particle;
   (b) a lactic acid bacteria; and
   (c) a bacteria of the Baciliaceae family,
   wherein the lactic acid bacteria and the bacteria of the Baciliaceae family are active upon re-hydration.

2. The fertilizer of claim 1, wherein the lactic acid bacteria is from a family selected from the group consisting of Lactobacillaceae, Streptococcaceae, Lactococcaceae, Leuconostocs and Bifidobacteriaceae.

3. The fertilizer of claim 1, wherein the lactic acid bacteria is from a species selected from the group consisting of *Lactobacillus acidophilus, Streptococcus lactis, Streptococcus cremoris, Streptococcus diacetylactis, Streptococcus thermophilus, Leuconostoc cremoris, Leuconostoc diacetylactis, Bifidobacterium lactis* and *Bifidobacterium brevis*.

4. The fertilizer of claim 1, wherein the lactic acid bacteria is from a *Lactobacillus acidophilus* species.

5. The fertilizer of claim 1, wherein the bacteria of the Baciliaceae family is from a species selected from the group consisting of *Bacillus subtilis* and *Bacillus licheniformis*.

6. The fertilizer of claim 1, the fertilizer further comprising a bacteria from the *Pseudomonas putida* species.

7. The fertilizer of claim 1, wherein the lactic acid bacteria and the bacteria of the Baciliaceae family are sprayed on the fertilizer particle.

8. The fertilizer of claim 7, wherein a first ferment comprising the lactic acid bacteria is sprayed on the fertilizer particle.

9. The fertilizer of claim 8, wherein the ratio (L/ton) between the first ferment and the fertilizer particle is about 1.

10. The fertilizer of claim 8, wherein the bacterial concentration of the first ferment is between about $10^7$ to about $10^{11}$ cells per ml.

11. The fertilizer of claim 8, wherein the bacterial concentration of the first ferment is between about $10^8$ to about $10^9$ cells per ml.

12. The fertilizer of claim 7, wherein a second ferment comprising the bacteria of the Baciliaceae family is sprayed on the fertilizer particle.

13. The fertilizer of claim 12, wherein the ratio (L/ton) between the second ferment and the fertilizer particle is about 1.

14. The fertilizer of claim 12, wherein the second ferment further comprises a bacteria of the *Pseudomonas putida* species.

15. The fertilizer of claim 12, wherein the bacterial concentration of the second ferment is between about $10^7$ to about $10^{11}$ cells per ml.

16. The fertilizer of claim 12, wherein the bacterial concentration of the second ferment is between about $10^8$ to about $10^9$ of cells per ml.

17. The fertilizer of claim 1, wherein the lactic acid bacteria and the bacteria of the Baciliaceae family are sprayed concurrently on the fertilizer particle.

18. The fertilizer of claim 1, wherein the lactic acid bacteria and the bacteria of the Baciliaceae family are sprayed independently on the fertilizer particle.

19. The fertilizer of claim 1, further comprising nutrients for the lactic acid bacteria and the bacteria of the Baciliaceae family.

20. The fertilizer of claim 1, wherein the plant is selected from the group consisting of hay, cotton, cauliflower, corn and soy.

21. The fertilizer of claim 1, wherein the lactic acid bacteria and the bacteria of the Baciliaceae family adhere directly to the fertilizer particle.

22. The fertilizer of claim 1, wherein the lactic acid bacteria and the bacteria of the Baciliaceae family are linked to a binder adhering to the fertilizer particle.

23. The fertilizer of claim 1, wherein the lactic acid bacteria and the bacteria of the Baciliaceae family are in their exponential growth phase.

24. A method for enhancing the growth, development or yield of a plant, said method comprising applying the fertilizer of claim 1 to a soil in the vicinity of the roots of the plant.

25. A method for enhancing the growth, development or yield of a plant, said method comprising applying the fertilizer of claim 1 under the seed of the plant.

26. A method of enhancing a soil for increasing growth, development or yield of a plant growing therein, the method comprising the step of adding to the soil the fertilizer of claim 1.

27. A composition for use with a fertilizer to enhance plant growth comprising a lactic acid bacteria and a bacteria of a Baciliaceae family, wherein the lactic acid bacteria and the bacteria of the Baciliaceae family adhere to a particle of the fertilizer and wherein the lactic acid bacteria and the bacteria of the Baciliaceae family are active upon re-hydration.

28. A soil additive to enhance plant growth, development or yield, the soil additive comprising a lactic acid bacteria and a bacteria of a Baciliaceae family, wherein the lactic acid bacteria and the bacteria of the Baciliaceae family adhere to a particle of a fertilizer and wherein the lactic acid bacteria and the bacteria of the Baciliaceae family are active upon re-hydration.

29. A method for producing a fertilizer, the method comprising mixing a fertilizer particle with a lactic acid bacteria and a bacteria of the Baciliaceae family, wherein the lactic acid bacteria and the bacteria of the Baciliaceae family are active upon re-hydration.

30. The method of claim 29, wherein a first ferment comprising the lactic acid bacteria is mixed with the fertilizer particle.

31. The method of claim 30, wherein the ratio (L/ton) between the first ferment and the fertilizer particle is about 1.

32. The method of claim 30, wherein the first ferment is cooled down prior to being mixed with the fertilizer particle.

33. The method of claim 32, wherein the first ferment is cooled down to between about 0° C. to about 12° C.

34. The method of claim 32, wherein the first ferment is cooled down to between about 0° C. to about 5° C.

35. The method of claim 30, wherein a second ferment comprising the bacteria of the Baciliaceae family is mixed with the fertilizer particle.

36. The method of claim 35, wherein the second ferment further comprises a bacteria of the *Pseudomonas putida* species.

37. The method of claim 35, wherein the ratio (L/ton) between the second ferment and the fertilizer particle is about 1.

38. The method of claim 35, wherein the second ferment is cooled down prior to being mixed with the fertilizer particle.

39. The method of claim 38, wherein the second ferment is cooled down to between about 0° C. to about 12° C.

40. The method of claim 38, wherein the second ferment is cooled down to between about 0° C. to about 5° C.

41. The method of claim 35, wherein the bacterial concentration of the second ferment is between about $10^7$ to about $10^{11}$ cells per ml.

42. The method of claim 35, wherein the bacterial concentration of the second ferment is between about $10^8$ to about $10^9$ cells per ml.

43. The method of claim 30, wherein the lactic acid bacteria and the bacteria of the Baciliaceae family are in their exponential growth phase.

44. The method of claim 30, wherein the bacterial concentration of the first ferment is between about $10^7$ to about $10^{11}$ cells per ml.

45. The method of claim 30, wherein the bacterial concentration of the first ferment is between about $10^8$ to about $10^9$ cells per ml.

46. The method of claim 30, wherein the lactic acid bacteria is from a family selected from the group consisting of Lactobacillaceae, Streptococcaceae, Lactococcaceae, Leuconostocs and Bifidobacteriaceae.

47. The method of claim 30, wherein the lactic acid bacteria is from a species selected from the group consisting of *Streptococcus lactis, Streptococcus cremoris, Streptococcus diacetylactis, Streptococcus thermophilus, Leuconostoc cremoris, Leuconostoc diacetylactis, Lactobacillus acidophilus, Bifidobacterium lactis* and *Bifidobacterium brevis*.

48. The method of claim 30, wherein the lactic acid bacteria is from a *Lactobacillus acidophilus* species.

49. The method of claim 30, wherein the bacteria of the Baciliaceae family is from a species selected from the group consisting of *Bacillus subtilis* and *Bacillus licheniformis*.

50. The method of claim 30, wherein nutrients for the lactic acid bacteria and the bacteria of a Baciliaceae family are mixed with the fertilizer particles.

51. The method of claim 30, wherein the lactic acid bacteria and the bacteria of a Baciliaceae family are sprayed on the fertilizer particles.

52. The method of claim 30, wherein the lactic acid bacteria and the bacteria of a Baciliaceae family are sprayed concurrently on the fertilizer particles.

53. The method of claim 30, wherein the lactic acid bacteria and the bacteria of a Baciliaceae family are sprayed independently on the fertilizer particles.

* * * * *